US00PP09394P

United States Patent [19]

Schumann et al.

[11] Patent Number: Plant 9,394

[45] Date of Patent: Dec. 5, 1995

[54] GERANIUM PLANT NAMED 'FISCOMEDY'

[75] Inventors: Ingeborg Schumann, Albstadt; Angelika Utecht, Montabaur, both of Germany

[73] Assignee: Florfis AG, Binningen, Switzerland

[21] Appl. No.: 360,344

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fiscomedy, particularly characterized by the combined features of purple violet flower color, double flower type, medium green foliage with weak zonation, vigorous growth and good branching ability, and medium, early flower response.

2 Drawing Sheets

The present invention comprises a new and distinct cultivar of geranium, botanically known as *Pelargonium peltatum l'Hert*, commonly refered to as ivy geranium, and referred to by the cultivar name Fiscomedy.

Fiscomedy is a product of a planned breeding program which had the objective of creating new geranium cultivars with pink flower color, compact growth habit and zoned leaves.

Fiscomedy was originated from a hybridization made by inventor Ingeborg Schumann in a controlled breeding program is Galdar, Gran Canaria, Spain in 1987. The female parent was an unnamed hybrid obtained by a series of crosses between the cultivars Rigi, characterized by pink semi-double flowers and vigorous but loose growth; Italian Gem, characterized by purple-pink flowers and dark green foliage with zonation; El Gaucho, characterized by salmon rose flowers and leaves without zonation; and Princeton, having pink flowers but also lacking zonation.

The male parent of Fiscomedy was Joseph Warren, characterized by pink flower color, foliage with zonation, and vigorous growth.

Fiscomedy was discovered and selected as one flowering plant within the progeny of the stated cross by Ingeborg Schumann in 1988 in a controlled environment in Galdar, Gran Canaria, Spain.

The first act of asexual reproduction of Fiscomedy was accomplished when vegetative cuttings were taken from the initial selection in autumn 1990 in a controlled environment in Galdar, Gran Canaria, Spain, by, or under the supervision of inventor Angelika Utecht.

Horticultural examination of plants grown from these cuttings initiated in May 1991, and continuing thereafter, has demonstrated that the combination of characteristics are herein disclosed for Fiscomedy are firmly fixed and are retained through successive generations of asexual reproduction.

Fiscomedy has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fiscomedy, which, in combination, distinguish this geranium as a new and distinct cultivar:

1. Purple violet flower color and double flower type.
2. Medium green leaves with weak zonation.
3. Vigorous growth habit with good branching ability.
4. Medium early flower response.

Of the many commercial cultivars known to the present inventors, the most similar in comparison to Fiscomedy is Fisjoy. Reference is made to attached Chart A which compares certain characteristics of Fiscomedy to those same characteristics of Fisjoy. In general comparison to Fisjoy, Fiscomedy has a flower color with more bluish tint, has double flower form, and larger leaves.

The accompanying color photographics drawing show typical flower and foliage characteristics of Fiscomedy, with colors being as true as possible with illustrations of this type.

The photo on sheet 1 is a perspective view of a mature plant in a hanging basket.

The photograph on sheet 2 shows flowers and foliage in more detail.

In the following description, color references are made to The Royal Horticultural Society Colour Chart. The color values were determined indoors in May from plants grown indoors in Hillscheid, Federal Republic of Germany.

Classification:

*Botanical.*—A hybrid of the species *Pelargonium peltatum l'Hert.*

*Commercial.*—Ivy geranium, cv., Fiscomedy.

Inflorescence

Umbel:

*Shape.*—Nearly semi-spherical.

*Average diameter.*—95 mm.

*Average depth.*—50 mm.

*Peduncle length.*—160 mm.

*Pedicel length.*—38 mm.

*Pedicel color.*—Green, partly light red.

*Number of flowers per umbel.*—7–10.

Corolla:

*Average diameter.*—52 mm.

Form.—Double.

*Number of petals.*—15–20.

*Number of petaloids.*—2–3.

*Color (general tonality from a distance of three meters).*—Purple violet.

*Color of upper petals.*—Between 74A and 78A.

*Color of lower petals.*—Between 74A and 78A.

*Markings on upper petals.*—Dark red, almost black veins.

*Color of lower surface of petals.*—78B.

*Color of sepals.*—Green, largest petal slightly infused with anthocyanin.

*Number of sepals.*—5–7.

Bud:

*Shape.*—Elliptical.

*Color (adaxial).*—Medium green.

*Color (abaxial).*—Violet.

Reproductive organs:

*Androecium.*—Few, often only 2–3 fertile anthers, pink filaments, orange pollen.

*Gynoecium.*—5–6 lobed stigma, violet pink style and stigma.

Spring flowering response period: In Hillscheid, Federal Republic of Germany, in 1993 plants had on average 0.5 flowers opened 15 weeks after planting of unrooted cuttings.

Outdoor flower production: The flower count in 1993 in Hillscheid, Federal Republic of Germany was between 40 and 54 flowers per plant for May through August observation period.

Durability: Shatter resistance good.

Plant

Foliage:

*Form.*—Ivy-shaped.

Margin.—Entire.

*Size of leaf.*—90 mm.

*Color of upper surface.*—Medium green, approximately 137C-D.

*Color (zonation).*—Brown 166A.

*Tolerance of botrytis.*—Average.

General Appearance and Form:

*Internode length.*—5–6 mm.

*Branching pattern.*—2.9 branches per week.

*Length.*—85 cm (in September, 35-week-old plants).

CHART A

| CHARACTERISTIC | FISCOMEDY | FISJOY |
|---|---|---|
| Flower color | 74A–78A | 74A |
| Number of petals per flower | 15–20 | 8–11 |
| Distinctness of zonation | Weak | Medium |

It is claimed:

1. A new and distinct cultivar of geranium plant named Fiscomedy, as illustrated and described.

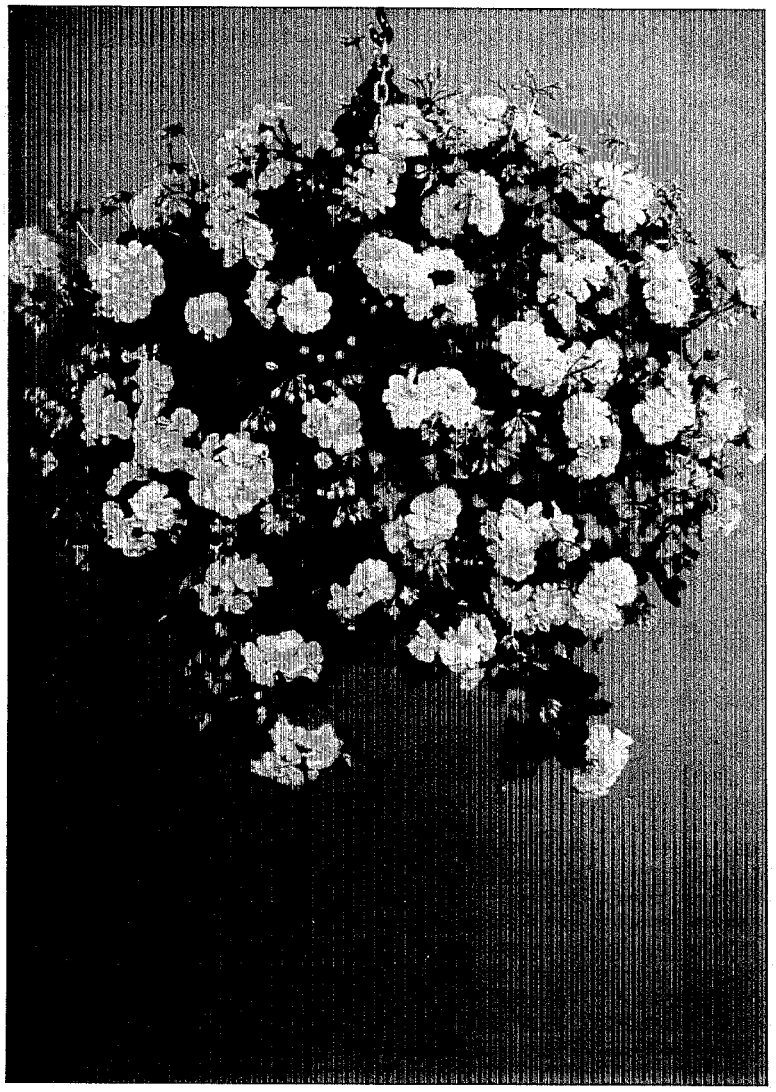

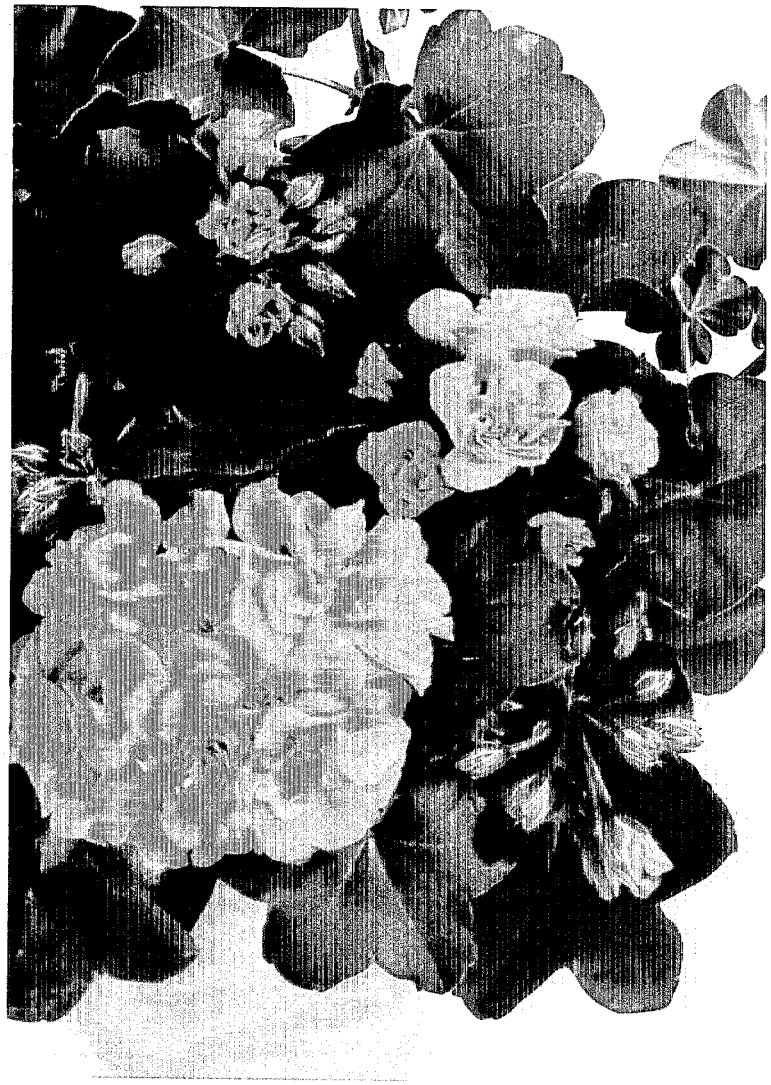

* * * * *